(12) United States Patent
Mitchell

(10) Patent No.: US 9,757,376 B2
(45) Date of Patent: *Sep. 12, 2017

(54) PHARMACEUTICAL COMPOSITIONS

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Arlington, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/287,047

(22) Filed: Oct. 6, 2016

(65) Prior Publication Data

US 2017/0020873 A1 Jan. 26, 2017

Related U.S. Application Data

(63) Continuation of application No. 14/733,731, filed on Jun. 8, 2015, now Pat. No. 9,463,191, which is a continuation of application No. 13/703,584, filed as application No. PCT/US2011/040231 on Jun. 13, 2011, now Pat. No. 9,050,289.

(60) Provisional application No. 61/354,053, filed on Jun. 11, 2010, provisional application No. 61/354,057, filed on Jun. 11, 2010, provisional application No. 61/354,061, filed on Jun. 11, 2010.

(51) Int. Cl.

| | |
|---|---|
| *A61K 31/505* | (2006.01) |
| *A61K 31/137* | (2006.01) |
| *A61K 31/167* | (2006.01) |
| *A61K 31/09* | (2006.01) |
| *A61K 31/495* | (2006.01) |
| *A61K 31/485* | (2006.01) |
| *A61K 31/135* | (2006.01) |
| *A61K 31/4402* | (2006.01) |
| *A61K 45/06* | (2006.01) |

(52) U.S. Cl.
CPC ............ *A61K 31/505* (2013.01); *A61K 31/09* (2013.01); *A61K 31/135* (2013.01); *A61K 31/137* (2013.01); *A61K 31/167* (2013.01); *A61K 31/4402* (2013.01); *A61K 31/485* (2013.01); *A61K 31/495* (2013.01); *A61K 45/06* (2013.01)

(58) Field of Classification Search
CPC .. A61K 31/505; A61K 31/495; A61K 31/137; A61K 31/09; A61K 31/485; A61K 31/167; A61K 31/4402
USPC .......... 514/255.04, 653, 275, 289, 357, 352; 564/355; 546/74; 544/396, 332
See application file for complete search history.

(56) References Cited

U.S. PATENT DOCUMENTS

| | | | |
|---|---|---|---|
| 9,050,289 B2* | 6/2015 | Mitchell | A61K 31/137 |
| 9,463,191 B2* | 10/2016 | Mitchell | A61K 31/137 |
| 2008/0014274 A1* | 1/2008 | Bubnis | A61K 31/137 424/486 |
| 2008/0026055 A1* | 1/2008 | Fubara | A61K 9/0056 424/464 |

* cited by examiner

Primary Examiner — Kristin Vajda
(74) Attorney, Agent, or Firm — Winstead PC

(57) ABSTRACT

A composition of an antitussive, a decongestant, or an antihistamine to treat upper respiratory and oral pharyngeal congestion and related symptoms in a patient.

5 Claims, No Drawings

PHARMACEUTICAL COMPOSITIONS

CROSS-REFERENCES TO RELATED APPLICATIONS

This Application is a continuation of application Ser. No. 14/733,731, filed Jun. 8, 2015, which is a continuation of application Ser. No. 13/703,584, filed Dec. 11, 2012, which is a US national stage application of PCT/US2011/040231 under 35 U.S.C. §371 filed Jun. 13, 2011, which claims priority from U.S. Provisional Patent Application No. 61/354,053 filed Jun. 11, 2010, U.S. Provisional Patent Application No. 61/354,057 filed Jun. 11, 2010, and U.S. 61/354,061 filed Jun. 11, 2010, all of which are hereby incorporated by reference as if fully set forth herein.

FIELD OF THE INVENTION

The present invention relates to the treatment and relief of various symptoms of upper respiratory and oral pharyngeal congestion, and in particular, to a combination medication for treatment and relief thereof.

BACKGROUND OF THE INVENTION

People around the world frequently suffer from upper respiratory tract and oral pharyngeal congestion. This congestion may be caused by allergies, infections in the respiratory tract and/or oral and pharyngeal cavities, changes in weather conditions, as well as from the overall health and genetic disposition of the person. This congestion is generally diagnosed from partially or fully blocked air passages including airways in the lungs, mouth, nose, and throat. Other symptoms related to the cause typically accompany the congestion. Cough, tickles in the throat, cold symptoms such as fever, flu, sinus infections, and throat or gland pain are some of the more common symptoms found with upper respiratory and oral pharyngeal congestion.

Congestion of the upper respiratory tract and oral pharyngeal cavity and related symptoms generally have undesirable effects for the afflicted person. For example, the congestion may affect performance in the workplace, school, and at home up to and including loss of work and loss of school attendance. Further, congestion may reduce the ability to perform routine activities, such as housework, driving, running errands, and may even totally incapacitate the person. Severe and intolerable congestion often requires visits to the hospital and treatment. In addition, viral or bacterial infections of the sinus passage or other airway may be passed to healthy persons through symptoms of the congestion. For example, a cough or sneeze may convey a *bacterium* or virus to another person. Thus, upper respiratory tract and oral pharyngeal congestion and its symptoms need to be treated.

Generally, there are two typical approaches to treating symptoms of the congestion. One approach involves initially treating the underlying cause of the symptom. For example, a bacterial infection is generally treated by administering an antibiotic to kill the bacteria causing the infection. The second approach involves treating the symptoms themselves, typically in addition to treating the underlying cause, by independently administering one or more medications for relief of specific symptoms. For example, an antitussive agent, commonly referred to as a cough suppressant, has been typically administered for the treatment or relief of cough. An opioid medication, such as codeine and hydrocodone bitartrate, has generally been administered to relieve pain consistent with the congestion while suppressing a cough. Also decongestants, such as phenylephrine and pseudoephedrine, have been administered to both children and adults in flavored formulations for reducing mucosal swelling and draining the mucus build-up to clear congestion in the air passages. Symptoms due to allergies or allergens are often treated with an antihistamine. Antihistamines, often referred to as histamine-class receptor blockers, are compounds that may antagonistically block the histamine receptor from binding histamine thereby preventing the symptoms of an allergy.

There are many different treatment medications utilizing a combination of agents in therapeutic doses for treating multiple symptoms of upper respiratory tract and oral pharyngeal congestion. As one example, a single medication may include an expectorant, in combination with an antitussive agent, for removing phlegm or mucus that may have accumulated in the lungs and other air passages in addition to suppressing a cough. The expectorant is helpful in preventing the progression of a mild case of bronchitis to a more severe case of pneumonia.

Combination therapy provides many benefits. For example, it allows patients suffering from congestion and related symptoms to take only a single dosage medication, as opposed to multiple medications, for relief therefrom. Further, it enhances compliance in accordance with a regimen by eliminating the need for the patient to take different medications. To this end, combination therapy provides convenience, ensures compliance, and saves cost.

Combined treatment medications may be formulated as syrups, pills, tablets, and capsules. Formulations may include flavoring agents to mask undesirable flavors or tastes from desired medicinal agents and colorants to render the medication more attractive and appealing to the eye. For example, many formulations have a raspberry, cherry, orange, or grape flavor well liked by both children and adults. Moreover, these flavors are easily identified by their color. In combination formulations, the individual ingredients are included in amounts proven to be effective to treat targeted symptoms. Effective amounts have varied depending on the particular formulation, type and degree of the symptoms, and desired user or consumer. For example, a child's dose of an elixir or syrup for the relief of cough and pain related to congestion may have the antitussive and analgesic in reduced quantities based on size, weight, and age of the child targeted, comparable to a composition or formulation for an adult which may have double the dosage of the antitussive and analgesic.

Accordingly, it is desirable to have an administrable composition to reduce symptoms of upper respiratory tract and oral pharyngeal congestion. It is further desirable that the composition be effective in reducing cough, congestion, histamine-stimulated allergy symptoms and related pain. Still further, it is desirable for the composition to contain dosages suitable for administration to a child as well as an adult. In addition, it is desirable to have the composition in a convenient and pharmaceutically acceptable dosage form.

SUMMARY OF THE INVENTION

The present invention provides compositions and methods for treating upper respiratory and oral pharyngeal congestion and related symptoms in a person suffering therefrom. To this end, and in accordance with the principles of the present invention, there is provided a composition of a decongestant, and an antihistamine. Optionally, a composition may include an antitussive, an expectorant and an analgesic. The combination of an antitussive, a decongestant, and an antihistamine in a single composition provides relief of cough, congestion in the air passageways, and common allergy-type symptoms resulting from exposure to various allergens, in a convenient and effective dosage formulation.

The composition is formulated in pharmaceutically acceptable forms such as liquids, pills, capsules, tablets, and the like. Suitable capsule forms include, without limitation, liquid gelatin capsules and enteric-coated capsules. The tablet form may be chewable, may melt or disintegrate in the mouth, or may be enteric-coated to provide delayed-release and sustained-release characteristics for the composition. In one embodiment, the composition is formulated into a liquid. The composition may further include other components, such as conventional excipients including binders, colorants, fragrances, and the like, to render the composition more attractive and suitable for use.

By virtue of the foregoing, there is thus provided compositions and methods for treating upper respiratory and oral pharyngeal congestion and related symptoms in effective formulations. These and other benefits and advantages of the present invention shall be made apparent from the accompanying detailed description thereof.

DETAILED DESCRIPTION OF EXEMPLARY EMBODIMENTS

The present invention provides compositions and methods for treating upper respiratory and oral pharyngeal congestion and related symptoms in a patient in need thereof. The term "upper respiratory and oral pharyngeal congestion" as used herein includes congestion in the oral, pharyngeal, nasal, and bronchial passages of the upper respiratory tract. It also is intended to include other symptoms, such as cough and pain related to allergies, infections, colds, coughs, flu, viral and bacterial infections, and other common causes for the congestion. Thus, multiple symptoms including congestion may be treated with the compositions of the present invention. Treatment includes a reduction in severity or duration, delay in onset, and/or general relief of one or more of these symptoms. The term is intended to refer to congestion as described herein, as well as to a wide range of symptoms related to the congestion or its cause and treatable with the present compositions. For example, symptoms related to a common cold or flu such as cough, fever, and the like, and allergy symptoms such as hives, breakouts, swelling, and runny nose due to external stimulants are treated with the present compositions. In addition, symptoms, such as congestion, cough, pain and discomfort associated with the congestion, resulting from a bacterial or viral infection, particularly an infection in the respiratory tract, are also treated with the present compositions. The term "congestion", as use herein, is intended to refer to the narrowing of an airway including the oral, pharyngeal, nasal and bronchial passages due to fluid or a solid substance, such as mucus or phlegm. Narrowing of the airway is often due to swelling or inflammation of the mucous membrane lining the passage to result in a partially or fully blocked passage. Severe cases of congestion often cause difficulties in breathing. Besides allergic reactions, infections, and common cold and flu, the symptoms described herein may also be due to poor health or a predisposition for the symptom through genetic make-up. The terms "treating" and "alleviating", as used herein with respect to upper respiratory and oral pharyngeal congestion and related symptoms, include any reduction in severity or duration, of any degree, of the congestion and/or one or more of the related symptoms. The terms also include any delays in onset of and any general relief from the congestion and/or one or more of the related symptoms. Thus, the present invention encompasses palliative compositions and methods.

To this end, and in accordance with the principles of the present invention, the compositions include an antitussive, a decongestant, and an antihistamine. Inclusion of an antihistamine, in combination with an antitussive and a decongestant provides relief of histamine-stimulated allergy symptoms in addition to relieving other symptoms, such as cough, congestion, swelling, and pain. These added benefits provide increased efficacy and translate into convenience and cost savings for the patient.

The present invention provides pharmaceutical compositions containing an antihistamine along with a decongestant and optionally an analgesic or an antitussive. The compositions of the invention may be administered in effective dosages for treating nasal congestion symptoms. To this end, the pharmaceutical compositions include at least one antihistamine and at least one stimulant. The most potent antihistamines are generally sedating in nature and the sedation is reduced or alleviated with the stimulant. The compositions are useful for treating allergic reactions and other histamine-mediated symptoms, as well as for providing other physiological effects including, for example, anticholinergic effects, analgesic effects, analgesic adjuvant effects, soporific effects, anti-secretory effects, and combination effects thereof. By combining a potent, effective antihistamine with an effective, anti-sedating stimulant, the compositions of the present invention may be administered more safely than prior art antihistamine-containing medications utilized for the same purpose. The present invention also provides methods of use for the pharmaceutical compositions.

Antihistamines suitable for the compositions include, without limitation, diphenhydramine, cyproheptadine hydrochloride, bromphenermine, hydroxyzine, chlorpheniramine, pyrilamine maleate, pyrilamine tannate, acepromazine, aceprometazine, alimemazine, alimemazine tartrate, amoxydramine camsilate, antazoline chlorhydrate, antazoline mesilate, antazoline phosphate, astemizole, azatadine dimaleate, azelastine hydrochloride, bamipine hydrochloride, benactyzine hydrochloride, bretylium tosilate, bromazine hydrochloride, brompheniramine maleate, buclizine dihydrochloride, bufexamac, carbinoxamine maleate acid, cetiedil citrate, cetirizine dihydrochloride, chlorcyclizine hydrochloride, chlorphenamine maleate, chlorphenoxamine hydrochloride, chlorprothixene hydrochloride, cinnarizine, clemastine fumarate, clemizole hexachlorophenate, clemizole penicilline, clemizole undecylenate, clocinizine dihydrochloride, clofedanol, clofenetamine hydrochloride, cyclizine hydrochloride, dexchlorpheniramine maleate, di (acefylline) diphenhydramine, difencloxazine, dimelazine hydrochloride, dimenhydrinate, dimethoxanate hydrochloride, cimetotiazine mesilate, diphenhydramine hydrochloride, diphenhydramine mesilate, diphenylpyraline hydrochloride, diproqualone camsilate, dixyrazine, doxylamine succinate, eprozinol dihydrochloride, etodroxizine dimaleate, etybenzatropine bromhydrate, etybenzatropine hydrochloride, etymemazine hydrochloride, fenethazine hydrochloride, fenoxazoline hydrochloride, fenpentadiol, flunarizine hydrochloride, flupentixol decanoate, flupentixol dihydrochloride, histapyrrodine hydrochloride, hydroxyzine dihydrochloride, hydroxyzine embonate, indoramine hydrochloride, isothipendyl hydrochloride, ketotifene fumarate, levocabastine hydrochloride, levomepromazine, levomepromazine hydrochloride, levomepromazine embonate, levomepromazine maleate, loratadine, maprotiline hydrochloride, maprotiline mesilate, maprotiline resinate, meclozine hydrochloride, mecysteine hydrochloride, medifoxamine fumarate, mefenidramium metilsulfate, mepyramine maleate, mequitazine, methaqualone, methdilazine hydrochloride, metixene hydrochloride, mizolastine, moxisylyte hydrochloride, niaprazine, orphenadrine hydrochloride, oxaflumazine disuccinate, oxatomide, oxolamine benzilate, oxolamine citrate, oxomemazine, oxomemazine hydrochloride, parathiazine teoclate, perimetazine, pheniramine maleate, phenoxybenzamine hydrochloride, phenyltoloxamine, phenyltoloxamine citrate, pimethixene, pipotiazine, pipretecol dihydrochloride, pizotifene malate, prednazoline, profenamine hydrochloride, promethazine, promethazine hydrochloride, promethazine embonate, promethazine polyvinylbenzene-metacrylate, propiomazine, terfenadine, thenalidine tartrate, thenyldiamine hydrochloride, thiazinamium metilsulfate, thonzylamine hydrochloride, tripelennamine hydrochloride, triprolidine hydrochloride, and tymazoline hydrochloride, and combinations thereof.

The antihistamine is included in an amount, per dosage of the composition, sufficient to alleviate one or more histamine-mediated responses in a patient. Effective doses of the antihistamine will generally vary depending upon the antihistamine (s) administered.

The present composition also includes an antitussive. The term "antitussive", as used herein, is intended to include any agent or active ingredient effective for cough suppression such as chlophedianol hydrochloride. These also include, but are not limited to, common opioid analgesics such as hydrocodone, codeine, morphine, morphine-related compounds including diacetylmorphine, oxymorphone, hydromorphone, dextromethorphan, levorphanol, oxycodone, nalmefene, methadone, meperidine, pentazocine, buprenorphine, nalbuphine, butorphanol, sufentanyl, alfentanyl and propoxyphene, and opioid antagonists not structurally-related to morphine, such as nalorphine, naloxone, naltrexone and fentanyl. In one embodiment, the antitussive agent is hydrocodone or a pharmaceutically acceptable salt form thereof, such as hydrocodone bitartrate.

The present composition also includes a decongestant. The term "decongestant" as used herein, is intended to refer to any agent or ingredient, active for reducing or eliminating congestion of the air passages by widening the airway, and/or by stimulating the release of phlegm and mucus from these passages. Air passages may be widened by reducing the swelling of the mucous membranes in the passage. Generally, sympathomimetic drugs have decongestant properties. Examples of suitable decongestants include, without limitation, phenylethylamine, epinephrine, norepinephrine, dopamine, dobutamine, colterol, ethylnorepinephrine, isoproterenol, isoetharine, metaproterenol, terbutaline, metaraminol, phenylephrine, tyraine, hydroxyamphetamine, ritodrine, prenalterol, methoxyamine, albuterol, amphetamine, methamphetamine, benzphetamine, ephedrine, phenylpropanolamine, mephentermine, phentermine, fenfluramine, propylhexedrine, diethylpropion, phenmetrazine, phendimetrazine, oxymetazoline, xylometazoline, and pseudoephedrine.

It should be understood that an effective amount of the antitussive and the decongestant generally vary with the particular antitussive and decongestant chosen. In addition, an effective amount depends upon many other factors, such as known differences in pharmacokinetic parameters (absorption, distribution and clearance) regardless of the cause. For example, in a patient with a renal dysfunction or disorder, the effective dose of the antihistamine, the antitussive, and the decongestant is generally half of an effective dose for a patient without renal dysfunction.

While the present composition includes an antitussive, a decongestant, and an antihistamine, the present composition is not so limited and may include other components. These components include conventional excipients, useful and/or desirable to render the composition suitable or attractive for consumption and use. Excipients providing physical and aesthetic properties for formulation or delivery of the composition are desirable. For example, with respect to physical properties, ingredients imparting desirable and acceptable hardness, disintegration properties, dissolution rate for release of therapeutic components, stability, and size to effectively deliver the composition may be included. Disintegrants may be included for the purposes of facilitating the breakup of a tablet after the tablet is administered to the patient. Examples of disintegrants include, but are not limited to, modified or unmodified starches such as cornstarch, potato starch, wheat starch, or sodium cross-carmellos. With respect to aesthetics, it may be desirable for the composition to contain additives that appeal to the human senses such as colorants, fragrances, texture modifiers, and/or flavorants. Additionally, many flavoring agents such as, for example, fruit flavors, or sweeteners, such as sodium saccharin, confectionery sugar, sucrose, xylitol, or combinations thereof, may be included. Additionally, suitable colorants including, for example, red beet powder, ferric oxide, FD&C dyes, or combinations thereof, may be included in the present compositions. Desirable excipients may also include buffering agents, surfactants, electrolytes, and thixotropic agents. It should be understood that these other components should not affect the action or mechanism of action of the antitussive, decongestant, and/or the antihistamine in the composition.

Excipients or formulations affecting the release properties, mechanisms, and/or rates of the antitussive, the decongestant, and the antihistamine, from the composition upon oral ingestion may be provided. For example, the composition may be formulated such that the release of the antitussive, the decongestant, and/or the antihistamine or other active ingredients from the composition is delayed for a period of time or to survive a particular environment.

Advantageously, the composition may be formulated so as to prevent the release of the antitussive, the decongestant, and/or the antihistamine in the stomach where they may likely be acidified, salted out and excreted from the body rather than absorbed into the circulation. For example, the composition may be coated with a coating to improve absorption and render the composition more bioavailable than it would otherwise be without the coating. Enteric coatings or encapsulation-type coatings as known to one skilled in the art are suitable for this purpose. In one embodiment, a table or a capsule form of the composition is enterically coated so as to provide delayed-release and sustained-release properties to the composition. Sustaining the release of individual active ingredients to the body over a period of time prolongs the effective time period of relief from the congestion and related symptoms, provided, however, the amount of the ingredient in the blood stream is within the effective therapeutic window for that particular ingredient. Further, preservatives may be provided to prevent degradation of components in the composition or degradation of the composition as a whole, thereby improving the stability and prolonging the shelf life of the composition.

The composition of the present invention may be formulated in a single form. In one embodiment, the form is convenient to swallow, and has a generally accepted appearance and taste to promote consumption and compliance with a dosing regimen. In accordance with one aspect of the present invention, the composition is formulated into a dosage form that may be an ingestible liquid, a pill, a tablet, a capsule, a suppository, etc. In accordance with another aspect of the invention, the composition may be formulated into a parenterally administrable form. It should be understood by one skilled in the art that certain active agents, such as hydrocodone, are typically not parenterally administered, such as by intra-venous administration. However, other opioids such as codeine, morphine, methadone, and fentanyl may be administered with antihistamine in a non-orally administrated formulation. In accordance with a further aspect of the invention, the present composition may include active ingredients suitable for sub-lingual administration. In accordance with yet another aspect of the invention, the present composition may be administered via mucous membranes of the buccal, nasal, rectal cavities, etc. The desired formulation may be prepared by a process known in the art of pharmaceutical manufacture. For example, liquid formulations may be prepared in the form of a syrup or a suspension. In one embodiment, the composition is formulated into an elixir or a syrup having a desirable flavor for easy, trouble-free administration to a child.

Solid formulations, such as capsules may be prepared by first blending the antitussive, the decongestant, and the antihistamine with other desirable additives and then filling capsular materials with the blended mixture using conventional filling equipment. In one embodiment, the capsular material is a gelatin. The capsule formed may be a liquid gelatin capsule. Further, where desired, the capsule may be coated for added benefits. In general, tablets may be formed by first blending the components and then either directly compressing the blended components, or granulating the components followed by compressing them into a tablet form. Additional ingredients may be included during compression where desired. For example, the granular mixture may contain one or more lubricants to inhibit sticking during compression. Examples of suitable lubricants include, but are not limited to, stearic acid, palmetic acid, stearates, talc, and oils.

The compositions of the invention may also be formulated as a powder or sprinkles.

To effectively suppress cough, relieve pain, and reduce mucus membrane swelling for reducing congestion and other blockage of air passages, the composition of the present invention includes the antitussive, the decongestant, and the antihistamine in amounts suitable for treating children and adults alike.

In yet another embodiment of the present invention, there is provided methods of alleviating symptoms of upper respiratory and oral pharyngeal congestion by orally administering to a patient in need thereof a single dose of a composition or formulation including an antitussive, a decongestant, and an antihistamine. The patient in need may be a child or an adult suffering from the congestion. Administration of the composition will depend upon the form of the composition. For example, a liquid formulation may be administered to a child in amounts smaller than that administered to an adult. Administration will also depend upon various other factors related to the patient. For example, age, health, weight, prior medical history, extent and degree of symptoms, and overall medical diagnosis will generally influence the amounts administered. The composition is generally administered for alleviating cough, pain, cold and allergy symptoms and also provides a sedative effect, an analgesic adjuvant effect, an anticholinergic affect, and a mild analgesic effect.

Formulations of the invention may contain any or all of the following in any combination: Purified Water; Any combination of permitted API's added as powders or as solutions, emulsions, suspensions: Chlophedianol Hydrochloride, Pseudoephedrine Hydrochloride, Phenylephrine, or any approved oral nasal decongestant; Dexchlorpheniramine Maleate, Dexbrompheniramine Maleate, Brompheniramine Maleate, Chlorcyclizine Hydrochloride, Thonzylamine Hydrochloride, Pyrilamine Maleate, Phenindamine Tartrate, or any approved oral antihistamine; Guaifenesin or any approved oral expectorant; Acetaminophen or any approved analgesic, antipyretic or anti-inflammatory; Citric Acid; Sodium Citrate; Propylene Glycol; Flavor; Sodium Saccharin Solution (Sodium Saccharin dissolved in water or any other solvent); Sorbitol; Glycerin; and Purified Water The formulations of the invention may be combined with any of the following pharmaceutical aids or excipients or preservatives, added as solutions, suspension, emulsions, or directly added as liquids or powders: Preservatives—including but not limited to the following: Parabens, Benzoates, Sorbates; Artificial Sweeteners—including but not limited to the following: Sucralose, Saccharin, Acesulfame; Sweeteners—including but not limited to the following: Sucrose, Corn Syrup, High Fructose Corn Syrup, Maltitol, Mannitol, Dextrose, Glucose; Thickeners—including but not limited to the following: Gums, Mucilages, Xanthan Gum, Guar Gum, Veegum, Methylcellulose Derivatives; Buffering Agents—including but not limited to the following: Phosphates, Citrates, Sulfates, Carbonates, etc.; Alcohol and Alcohol Derivatives as Solvents, Preservatives, Flavors; Emulsifiers; Coloring Agents, Dyes, Certified Colors; Any and all pharmaceutical excipients While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is, therefore, not limited to the specific details, representative method, and illustrated examples described. Accordingly, departures may be made from such details without departing from the scope or spirit of Applicant's general inventive concept.

Examples of the compositions of the invention are set forth below:

| ACTIVE 1 | ACTIVE 2 | ACTIVE 3 |
| --- | --- | --- |
| Chlophedianol HCl 12.5 mg | Pseudoephedrine HCl 30 mg | Dexchlorpheniramine Maleate 1 mg |
| Chlophedianol HCl 12.5 mg | Pseudoephedrine HCl 30 mg | Guaifenesin 100 mg |
| Chlophedianol HCl 12.5 mg | Pseudoephedrine HCl 30 mg | Guaifenesin 200 mg |
| Chlophedianol HCl 12.5 mg | Pseudoephedrine HCl 30 mg | Chlorcyclizine 9.375 mg |

-continued

| ACTIVE 1 | ACTIVE 2 | ACTIVE 3 |
|---|---|---|
| Chlorcyclizine HCl 9.375 mg | Pseudoephedrine HCl 30 mg | |
| Chlophendianol HCl 25 mg | Guaifenesin 200 mg | |
| Chlorcyclizine HCl 9.375 mg | Pseudoephedrine HCl 30 mg | |
| Chlorcyclizine HCl 9.375 mg | Pseudoephedrine HCl 30 mg | Codeine Phosphate 10 mg |
| Chlorcyclizine HCl 9.375 mg | Codeine Phosphate 10 mg | |
| Chlophedianol HCl 12.5 mg | Dexbrompheniramine 1 mg | Phenylephrine HCl 5 mg |
| Chlophedianol HCl 25 mg | Pseudoephedrine HCl 60 mg | Chlorpheniramine Maleate 4 mg |
| Chlorcyclizine HCl 9.375 mg | Pseudoephedrine HCl 30 mg | Chlophedianol HCl 12.5 mg |
| Chlorcyclizine HCl 9.375 mg | Pseudoephedrine HCl 30 mg | Dextromethorphan HBr 15 mg |
| Chlophedianol HCl 12.5 mg | Guaifenesin 100 mg | Phenylephrine HCl 5 mg |
| Thonzylamine HCl 50 mg | Codeine Phosphate 10 mg | |
| Thonzylamine HCl 50 mg | Codeine Phosphate 10 mg | Pseudoephedrine HCl 30 mg |
| Chlophedianol HCl 12.5 mg | Pseudoephedrine HCl 30 mg | |
| Chlophedianol HCl 12.5 mg | Dexbrompheniramine 1 mg | Phenylephrine HCl 5 mg |
| Chlophedianol HCl 12.5 mg | Pseudoephedrine HCl 30 mg | Brompheniramine Maleate 2 mg |
| Chlophedianol HCl 12.5 mg | Pseudoephedrine HCl 30 mg | Chlorcyclizine 9.375 mg |
| Chlophedianol HCl 25 mg | Pseudoephedrine HCl 60 mg | Chlorcyclizine 18.75 mg |
| Chlophedianol HCl 12.5 mg | Phenylephrine HCl 5 mg | Chlorcyclizine 9.375 mg |
| Chlophedianol HCl 25 mg | Phenylephrine HCl 10 mg | Chlorcyclizine 18.75 mg |
| Chlophendianol HCl 25 mg | Pseudoephedrine HCl 60 mg | Pyrilamine maleate 50 mg |
| Chlophendianol HCl 25 mg | Phenylephrine HCl 10 mg | Guaifenesin 200 mg |
| Chlophendianol HCl 25 mg | Phenylephrine HCl 10 mg | Guaifenesin 400 mg |
| Chlophendianol HCl 12.5 mg | Guaifenesin 100 mg | |
| Chlophendianol HCl 12.5 mg | Pseudoephedrine HCl 30 mg | Thonzylamine HCl 50 mg |
| Chlophendianol HCl 25 mg | Pseudoephedrine HCl 60 mg | Thonzylamine HCl 100 mg |
| Chlophendianol HCl 12.5 mg | Phenylephrine HCl 5 mg | Thonzylamine HCl 50 mg |
| Chlophendianol HCl 25 mg | Phenylephrine HCl 10 mg | Thonzylamine HCl 100 mg |
| Chlophendianol HCl 25 mg | Guaifenesin 400 mg | |
| Chlophendianol HCl 25 mg | Pseudoephedrine HCl 60 mg | Guaifenesin 400 mg |
| Chlorcyclizine HCl 9.375 | Phenylephrine HCl 5 mg | |
| Chlorcyclizine HCl 18.75 mg | Phenylephrine HCl 10 mg | |
| Chlorcyclizine HCl 18.75 mg | Pseudoephedrine HCl 60 mg | |
| Thonzylemine HCl 50 mg | Pseudoephedrine HCl 30 mg | |
| Thonzylemine HCl 100 mg | Pseudoephedrine HCl 60 mg | |
| Thonzylemine HCl 50 mg | Phenylephrine HCl 5 mg | |
| Thonzylemine HCl 100 mg | Phenylephrine HCl 10 mg | |
| Chlorcyclizine HCl 9.375 mg | Pseudoephedrine HCl 30 mg | Acetaminophen 325 mg |
| Thonzylamine HCl 50 mg | Pseudoephedrine HCl 30 mg | Acetaminophen 325 mg |
| Chlorcyclizine HCl 18.75 mg | Pseudoephedrine HCl 60 mg | Acetaminophen 500 mg |
| Thonzylamine HCl 100 mg | Pseudoephedrine HCl 60 mg | Acetaminophen 500 mg |
| Chlophendianol HCl 12.5 mg | Pseudoephedrine HCl 30 mg | Thonzylamine HCl 50 mg |
| Chlophendianol HCl 25 mg | Pseudoephedrine HCl 60 mg | Thonzylamine HCl 100 mg |
| Chlophendianol HCl 12.5 mg | Phenylephrine HCl 5 mg | Thonzylamine HCl 50 mg |
| Chlophendianol HCl 25 mg | Phenylephrine HCl 10 mg | Thonzylamine HCl 100 mg |
| Chlophendianol HCl 12.5 mg | Phenylephrine HCl 5 mg | Chlorcyclizine HCl 9.375 mg |
| Chlophendianol HCl 25 mg | Phenylephrine HCl 10 mg | Chlorcyclizine HCl 18.75 mg |
| Chlophendianol HCl 25 mg | Pseudoephedrine HCl 60 mg | Guaifenesin 200 mg |
| Chlophendianol HCl 25 mg | Phenylephrine HCl 10 mg | Brompheniramine 4 mg |
| Chlorcyclizine HCl 9.375 mg | Codeine Phosphate 10 mg | Pseudoephedrine HCl 30 mg |
| Chlorcyclizine HCl 9.375 mg | Codeine Phosphate 10 mg | Acetaminophen 325 mg |
| Thonzylamine HCl 50 mg | Codeine Phosphate 10 mg | Pseudoephedrine HCl 30 mg |
| Thonzylamine HCl 50 mg | Codeine Phosphate 10 mg | Acetaminophen 325 mg |
| Thonzylamine HCl 50 mg | Codeine Phosphate 10 mg | Phenylephrine HCl 5 mg |
| Chlorcyclizine HCl 9.375 mg | Codeine Phosphate 10 mg | Phenylephrine HCl 5 mg |
| Chlorcyclizine HCl 9.375 mg | Codeine Phosphate 10 mg | Phenylephrine HCl 5 mg |
| Thonzylamine HCl 50 mg | Codeine Phosphate 10 mg | Phenylephrine HCl 5 mg |
| Chlophendianol HCl 12.5 mg | Pseudoephedrine HCl 30 mg | Chlorpheniramine Maleate 2 mg |
| Chlophendianol HCl 12.5 mg | Pseudoephedrine HCl 30 mg | Dexbrompheniramine Maleate 1 mg |
| Thonzylamine HCl 50 mg | Pseudoephedrine HCl 30 mg | Dextromethorphan HBr 15 mg |
| Thonzylamine HCl 50 mg | Phenylephrine HCl 5 mg | Dextromethorphan HBr 15 mg |
| Chlorcyclizine HCl 9.375 mg | Pseudoephedrine HCl 30 mg | Dextromethorphan HBr 15 mg |
| Chlorcyclizine HCl 9.375 mg | Phenylephrine HCl 5 mg | Dextromethorphan HBr 15 mg |
| Chlophedinol HCl 12.5 mg | Pseudoephedrine HCl 30 mg | Guaifenesin 75 mg |
| Chlorcyclizine HCl 9.375 mg | Pseudoephedrine HCl 30 mg | Dextromethorphan HBr 15 mg |
| Thonzylamine HCl 50 mg | Phenylephrine HCl 5 mg | Dextromethorphan HBr 15 mg |
| Chlophendianol HCl 12.5 mg | Phenylephrine HCl 5 mg | Guaifenesin 200 mg |
| Chlophendianol HCl 12.5 mg | Pseudoephedrine HCl 30 mg | Pyrilamine Maleate 25 mg |
| Chlophendianol HCl 12.5 mg | Phenylephrine HCl 5 mg | Pyrilamine Maleate 25 mg |
| Chlophendianol HCl 12.5 mg | Pseudoephedrine HCl 30 mg | Guaifenesin 100 mg |

-continued

| ACTIVE 1 | ACTIVE 2 | ACTIVE 3 |
|---|---|---|
| Chlophendianol HCl 25 mg | Pseudoephedrine HCl 60 mg | Guaifenesin 200 mg |
| Chlophendianol HCl 12.5 mg | Phenylephrine HCl 5 mg | Guaifenesin 100 mg |
| Chlophendianol HCl 25 mg | Phenylephrine HCl 10 mg | Guaifenesin 200 mg |
| Chlophendianol HCl 25 mg | Pseudoephedrine HCl 60 mg | Guaifenesin 400 mg |
| Chlophendianol HCl 25 mg | Phenylephrine HCl 10 mg | Guaifenesin 400 mg |
| Chlophendianol HCl 12.5 mg | Pseudoephedrine HCl 30 mg | Guaifenesin 200 mg |
| Chlophendianol HCl 12.5 mg | Phenylephrine HCl 5 mg | Guaifenesin 200 mg |
| Chlophendianol HCl 12.5 mg | Pseudoephedrine HCl 30 mg | Doxylamine Succinate 6.25 mg |
| Chlophendianol HCl 12.5 mg | Pseudoephedrine HCl 30 mg | Doxylamine Succinate 6.25 mg |
| Chlophendianol HCl 12.5 mg | Phenylephrine HCl 5 mg | Doxylamine Succinate 6.25 mg |
| Chlophendianol HCl 12.5 mg | Phenylephrine HCl 5 mg | Doxylamine Succinate 6.25 mg |
| Chlophendianol HCl 12.5 mg | Pseudoephedrine HCl 30 mg | Diphenhydramine HCl 25 mg |
| Chlophendianol HCl 12.5 mg | Phenylephrine HCl 5 mg | Diphenhydramine HCl 25 mg |
| Chlophendianol HCl 12.5 mg | Pseudoephedrine HCl 30 mg | Diphenhydramine HCl 25 mg |
| Chlophendianol HCl 12.5 mg | Phenylephrine HCl 5 mg | Diphenhydramine HCl 25 mg |
| Chlophendianol HCl 12.5 mg | Guaifenesin 200 mg | |
| Chlophendianol HCl 8.33 mg | Brompheniramine 1.33 mg | Phenylephrine 33.33 mg |
| Chlorcyclizine HCl 25 mg | Pseudoephedrine HCl 60 mg | Codeine Phosphate 10 mg |
| Thonzylamine HCl 100 mg | Pseudoephedrine HCl 60 mg | Codeine Phosphate 10 mg |
| Chlorcyclizine HCl 25 mg | Pseudoephedrine HCl 60 mg | |
| Chlorcyclizine HCl 25 mg | | |
| Chlophedianol HCl 25 mg | Chlorcyclizine HCl 25 mg | |
| Chlophedinol HCl 25 mg | Pseudoephedrine HCl 60 mg | Chlorcyclizine HCl 25 mg |
| Chlophedianol HCl 12.5 mg | | |
| Chlophedianol HCl 25 mg | | |
| Thonzylamine HCl 100 mg | Codeine Phosphate 10 mg | |
| Thonzylamine HCl 100 mg | Pseudoephedrine HCl 60 mg | Dextromethorphan HBr 30 mg |
| Thonzylamine HCl 100 mg | Pseudoephedrine HCl 60 mg | Dextromethorphan HBr 15 mg |
| Thonzylamine HCl 100 mg | Pseudoephedrine HCl 60 mg | Dextromethorphan HBr 20 mg |
| Chlorcyclizine HCl 25 mg | Pseudoephedrine HCl 60 mg | Dextromethorphan HBr 30 mg |
| Dextromethorphan HBr 15 mg | Chlorcyclizine HCl 9.373 | |
| Dextromethorphan HBr 30 mg | Chlorcyclizine HCl HBr 18.75 mg | |
| Dextromethorphan HBr 15 mg | Thonzylamine HCl 50 mg | |
| Dextromethorphan HBr 30 mg | Thonzylamine HCl 100 mg | |
| Chlophedianol HCl 12.5 mg | Thonzylamine HCl 50 mg | |
| Chlophedianol HCl 12.5 mg | Chlorcyclizine HCl 9.375 mg | |

What is claimed is:

1. A pharmaceutical composition for alleviating symptoms of upper respiratory and oral-pharyngeal congestion in a subject, the composition comprising:
a first active ingredient comprising at least one of chlophedianol hydrochloride, chlorcyclizine hydrochloride, phenylephrine hydrochloride, dextromethorphan hydrobromide and thonzylamine hydrochloride, morphine, diacetylmorphine, oxymorphone, hydromorphone, dextromethorphan, levorphanol, oxycodone, nalmefene, methadone, meperidine, pentazocine, buprenorphine, nalbuphine, butorphanol, sufentanyl, alfentanyl, propoxyphene, nalorphine, naloxone, naltrexone and fentanyl;
a second active ingredient selected from the group consisting of hydroxyzine, chlorpheniramine, acepromazine, aceprometazine, alimemazine, alimemazine tartrate, amoxydramine camsilate, antazoline chlorhydrate, antazoline mesilate, antazoline phosphate, bamipine hydrochloride, benactyzine hydrochloride, bretylium tosilate, bromazine hydrochloride, buclizine dihydrochloride, bufexamac, chlorphenamine maleate, chlorphenoxamine hydrochloride, chlorprothixene hydrochloride, cinnarizine, clemastine fumarate, clemizole hexachlorophenate, clemizole penicilline, clemizole undecylenate, clocinizine dihydrochloride, clofedanol, clofenetamine hydrochloride, difencloxazine, dimelazine hydrochloride, dimenhydrinate, dimethoxanate hydrochloride, cimetotiazine mesilate, diphenylpyraline hydrochloride, diproqualone camsilate, dixyrazine, eprozinol dihydrochloride, etodroxizine dimaleate, etybenzatropine bromhydrate, etybenzatropine hydrochloride, etymemazine hydrochloride, fenethazine hydrochloride, fenoxazoline hydrochloride, fenpentadiol, flunarizine hydrochloride, flupentixol decanoate, flupentixol dihydrochloride, histapyrrodine hydrochloride, hydroxyzine dihydrochloride, hydroxyzine embonate, indoramine hydrochloride, isothipendyl hydrochloride, levomepromazine, levomepromazine hydrochloride, levomepromazine embonate, levomepromazine maleate, maprotiline hydrochloride, maprotiline mesilate, maprotiline resinate, meclozine hydrochloride, mecysteine hydrochloride, medifoxamine fumarate, mefenidramium metilsulfate, mepyramine maleate, mequitazine, methaqualone, methdilazine hydrochloride, metixene hydrochloride, moxisylyte hydrochloride, niaprazine, orphenadrine hydrochloride, oxaflumazine disuccinate, oxatomide, oxolamine benzilate, oxolamine citrate, oxomemazine, oxomemazine hydrochloride, parathiazine teoclate, perimetazine, phenoxybenzamine hydrochloride, phenyltoloxamine, phenyltoloxamine citrate, pimethixene, pipotiazine, pipretecol dihydrochloride, pizotifene malate, prednazoline, profenamine hydrochloride, promethazine, promethazine hydrochloride, promethazine embonate, promethazine polyvinylbenzene-metacrylate, propiomazine, thenalidine tartrate, thenyldiamine hydrochloride, and thiazinamium metilsulfate.

2. The pharmaceutical composition of claim 1, further comprising a third active ingredient selected from the group consisting of phenylethylamine, epinephrine, norepinephrine, dopamine, dobutamine, colterol, ethylnorepinephrine, isoproterenol, isoetharine, metaproterenol, terbutaline, metaraminol, phenylephrine, tyraine, hydroxy amphetamine, ritodrine, prenalterol, methoxyamine, albuterol, amphetamine, methamphetamine, benzphetamine, ephedrine, phenylpropanolamine, mephentermine, phentermine, fenfluramine, propylhexedrine, diethylpropion, phenmetrazine, phendimetrazine, oxymetazoline, and xylometazoline.

3. The pharmaceutical composition of claim 1, wherein the first active ingredient is present at a range of 9.375 mg to 100 mg.

4. The pharmaceutical composition of claim 1, wherein the second active ingredient is present at a range of 1 mg to 100 mg.

5. The pharmaceutical composition of claim 2, wherein third active ingredient is present at a range of 1 mg to 500 mg.

* * * * *